US006146854A

United States Patent [19]
Koster et al.

[11] Patent Number: 6,146,854
[45] Date of Patent: *Nov. 14, 2000

[54] FILTRATION PROCESSES, KITS AND DEVICES FOR ISOLATING PLASMIDS

[75] Inventors: Hubert Koster, Concord, Mass.; Andreas Ruppert, Linden, Germany

[73] Assignee: Sequenom, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/521,638

[22] Filed: Aug. 31, 1995

[51] Int. Cl.[7] .................................................. C12N 15/10
[52] U.S. Cl. ..................................... 435/91.1; 435/320.1
[58] Field of Search .......................... 435/6, 91.1, 287.2, 435/288.7, 91.2, 320.1; 436/173; 536/25.3, 25.4, 25.34, 26.5, 23.1; 935/77, 78

[56] References Cited

U.S. PATENT DOCUMENTS

| | | | |
|---|---|---|---|
| 4,139,346 | 2/1979 | Rabbani et al. | 422/56 |
| 4,214,159 | 7/1980 | Hillenkamp et al. | 250/288 |
| 4,237,234 | 12/1980 | Meunier | 435/301 |
| 4,442,354 | 4/1984 | Hurst et al. | 250/281 |
| 4,468,464 | 8/1984 | Cohen et al. | 435/317 |
| 4,725,677 | 2/1988 | Koster et al. | 536/27 |
| 4,740,470 | 4/1988 | Cohen et al. | 435/172.3 |
| 4,778,993 | 10/1988 | Waugh | 250/287 |
| 4,843,003 | 6/1989 | Henikoff et al. | 435/91 |
| 4,902,481 | 2/1990 | Clark et al. | 422/101 |
| 4,920,264 | 4/1990 | Becker | 250/282 |
| 4,948,442 | 8/1990 | Manns | 156/73.1 |
| 5,045,694 | 9/1991 | Beavis et al. | 250/287 |
| 5,047,215 | 9/1991 | Manns | 422/101 |
| 5,062,935 | 11/1991 | Schlag et al. | 204/157.41 |
| 5,118,937 | 6/1992 | Hillenkamp et al. | 250/282 |
| 5,135,870 | 8/1992 | Williams et al. | 436/173 |
| 5,187,083 | 2/1993 | Mullis | 435/91 |
| 5,202,561 | 4/1993 | Giessmann et al. | 250/281 |
| 5,210,412 | 5/1993 | Levis et al. | 250/288 |
| 5,234,824 | 8/1993 | Mullis et al. | 435/91 |
| 5,373,156 | 12/1994 | Franzen | 250/288 |
| 5,376,788 | 12/1994 | Standing et al. | 250/287 |
| 5,380,833 | 1/1995 | Urdea et al. | 536/22.1 |
| 5,381,008 | 1/1995 | Tanner et al. | 250/288 |
| 5,382,793 | 1/1995 | Weinberger et al. | 250/288 |
| 5,503,980 | 4/1996 | Cantor | 435/6 |
| 5,510,613 | 4/1996 | Reilly et al. | 250/287 |
| 5,547,835 | 8/1996 | Köster et al. | 435/6 |
| 5,580,733 | 12/1996 | Levis et al. | 435/6 |
| 5,605,798 | 2/1997 | Koster et al. | 435/6 |
| 5,622,824 | 4/1997 | Koster et al. | 435/6 |
| 5,625,184 | 4/1997 | Vestal et al. | 250/287 |
| 5,627,369 | 5/1997 | Vestal et al. | 250/287 |
| 5,631,134 | 5/1997 | Cantor | 435/6 |
| 5,641,959 | 6/1997 | Holle et al. | 250/287 |
| 5,654,545 | 8/1997 | Holle et al. | 250/287 |
| 5,691,141 | 11/1997 | Koster et al. | 435/6 |
| 5,700,642 | 12/1997 | Monforte . | |
| 5,742,049 | 4/1998 | Holle et al. | 250/282 |
| 5,760,393 | 6/1998 | Vestal et al. | 250/282 |
| 5,777,324 | 7/1998 | Hillenkamp | 250/288 |
| 5,777,325 | 7/1998 | Weinberger et al. | 250/287 |
| 5,795,714 | 8/1998 | Cantor et al. | 435/6 |
| 5,830,655 | 11/1998 | Monforte et al. | 435/6 |
| 5,869,242 | 2/1999 | Kamb | 435/6 |
| 5,885,775 | 3/1999 | Haff et al. | 435/6 |

FOREIGN PATENT DOCUMENTS

| | | |
|---|---|---|
| 5992994 | 8/1994 | Australia . |
| 6411694 | 10/1994 | Australia . |
| 0245945 | 11/1987 | European Pat. Off. ........ C12N 15/00 |
| 0 376 080 | 7/1990 | European Pat. Off. . |
| 0 517 515 | 12/1992 | European Pat. Off. . |
| 6-253842 | 9/1994 | Japan ............................ C12N 15/10 |
| 9014148 | 11/1990 | WIPO . |
| 9112341 | 8/1991 | WIPO . |
| 9213629 | 8/1992 | WIPO . |
| 9411530 | 5/1994 | WIPO . |
| 9416101 | 7/1994 | WIPO . |
| 9421822 | 9/1994 | WIPO . |
| 9507361 | 3/1995 | WIPO . |
| 9629431 | 9/1996 | WIPO . |
| 9632504 | 10/1996 | WIPO . |
| 9636731 | 11/1996 | WIPO . |
| 9636986 | 11/1996 | WIPO . |
| 9636987 | 11/1996 | WIPO . |
| 9708306 | 3/1997 | WIPO . |
| 9716699 | 5/1997 | WIPO . |
| 9737041 | 10/1997 | WIPO . |
| 9742348 | 11/1997 | WIPO . |
| 9743617 | 11/1997 | WIPO . |
| 9820019 | 5/1998 | WIPO . |
| 9820020 | 5/1998 | WIPO . |
| 9820166 | 5/1998 | WIPO . |

OTHER PUBLICATIONS

Miketova et al. Molecular Biotechnology 8:249–253, 1997.

Murray, K.K. Journal of Mass Spectrometry 31:1203–1215, 1996.

Alderton, Robert P. et al., "Magnetic Bead Purification of M13 DNA Sequencing Templates", *Analytical Biochemistry*, (1992), vol. 201, pp. 166–169.

Birnboim, H.C. et al., "A Rapid Alkaline Extraction Procedure for Screening Recombinant Plasmid DNA", *Nucleic Acids Research*, (1979), vol. 7, No. 6, pp. 1513–1523.

Ish–Horowicz, D. et al., "Rapid and Efficient Cosmid Cloning", *Nucleic Acids Research*, (1981), vol. 9, No. 13, pp. 2989–2998.

Kieser, T., "Factors Affecting the Isolation of CCC DNA from *Streptomyces lividans* and *Escherichia coli*", *Plasmid*, (1984), vol. 12, pp. 19–36.

Pierce ImmunoTechnology '93 Catalog, p. 57.

Qiagen Catalog (Feb. 1991), pp. 6–7.

(List continued on next page.)

*Primary Examiner*—Mary E. Mosher
*Attorney, Agent, or Firm*—Stephanie L. Seidman; Heller Ehrman White & McAuliffe LLP

[57] ABSTRACT

Processes, kits and preferred devices for rapidly isolating large numbers of plasmid DNAs from plasmid containing cells and for performing high throughput DNA sequencing are described.

37 Claims, 3 Drawing Sheets

OTHER PUBLICATIONS

Zimmermann, J. et al., "Automated Preparation and Purification of M13 Templates for DNA Sequencing", *Methods in Molecular and Cellular Biology*, (Jan./Feb. 1989), vol. 1, No. 1, pp. 29–34.

Ruppert, A., et al. (1995) "A Filtration Method for Plasmid Isolation Using Microtiter Filter Plates", *Analytical Biochemistry*, vol. 230, pp. 130–134.

Andersen, et al., Electrospray ionization and matrix assisted laser desorption/ionization mass spectrometry: Powerful analytical tools in recombinant protein chemistry, *Nature Biotech.* 14:449–457 (1996).

Ardey, Electrospray mass spectrometry, *Spectroscopy Europe*, 4:10–20 (1992).

Arlinghaus et al., "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Francis Barany, Genetic disease detection and DNA amplification using cloned thermostable ligase, *Proc. Natl. Acad. Sci. USA* 88:189–193 (1991).

Beck et al., Applications of dioxetane chemiluminescent probes to molecular biology, *Anal. Chem.* 62:2258–2270 (1990).

Beck et al., Chemiluminescent detection of DNA: application for DNA sequencing and hybridization, *Nucl Acids Res* 17:5115–5123 (1989).

Braun et al., Detecting CFTR gene mutations by using primer oligo base extension and mass spectrometry, *Clinical Chemistry* 43:1151–1158 (1997).

Braun et al., Improved Analysis of Microsatellites Using Mass Spectrometry, *Genomics* 46:18–23(1997).

Broude et al., Enhanced DNA sequencing by hybridization, *Proc. Natl. Acad. Sci. USA* 91:3072–3076 (1994).

Caldwell et al., Mid–infrared matrix assisted laser desorption ionization with a water/glycerol matrix, *Applied Surface Science* 127–129:242–247 (1998).

Chang, et al., Nucleotide sequence of the Alkaline phosphatase gene of *Excherichia coli Gene* 44:121–125 (1986).

Chen and Seeburg, Supercoil sequencing: A fast and simple method for sequencing plasmid DNA, *DNA* 4(2):165–170 (1985).

Covey, et al., The determination of protein, oligonucleotide and peptide molecular weights by ion–spray mass spectrometry, *Rapid Comm. Mass Spectrom.* 2:249–256 (1988).

Crain, Mass spectrometric techniques in nucleic acid research, *Mass Spectrom. Rev.* 9:505–554 (1990).

Eckstein (ed.), *Oligonucleotides and Analogues*, IRL Press, Oxford (1991).

Edmonds et al., Thermospray liquid chromatography–mass spectrometry of nucleosides and of enzymatic hydrolysates of nucleic acids, *Nucleic Acids Research* 13:8197–8206 (1985).

Ehring et al., Photochemical versus thermal mechanisms in matrix–assisted laser desorption/ionization probed by back side desorption, *Rapid Comm in Mass Spect* 10:821–824 (1996).

Eperon, I.C., Rapid preparation of bacteriophage DNA for sequence analysis in sets of 96 clones, using filtration, *Anal. Biochem* 156:406–412 (1986).

Fu et al., A DNA sequencing strategy that requires only five bases of known terminal sequenec for priming, *Proc. Natl. Acad. Sci. USA* 92:10162–10166 (1995).

Fu et al., A DNA sequencing strategy which requires only five bases of known terminal sequence for priming, Paper presented, Genome Mapping and Sequencing, Cold Spring Harbor Laboratory.

Fu et al., Efficient preparation of short DNA sequence ladders potentially suitable for MALDI–TOF DNA sequencing, *Genetic Analysis* 12:137–142 (1996).

Fu et al., Sequencing double–stranded DNA by strand displacement, *Nucl Acids Res* 25:677–679 (1997).

Fu et al., Sequencing exons 5 to 8 of the p53 gene by MALDI–TOF mass spectrometry, *Nat Biotechnol* 16:381–4 (1998).

Ganem et al., Detection of oligonucleotide duplex forms by ion–spray mass spectrometry, *Tetrahedron Letters* 34:1445–1448, (1993).

Gildea et al., A versatile acid–labile linker for modification of synthetic biomolecules, *Tetrahedron Letters* 31:7095–7398 (1990).

Gross et al., Investigations of the metastable decay of DNA under ultraviolet matrix–assisted laser desorption/ionization conditions with post–source–decay analysis and hydrogen/deuterium exchange, *J Amer Soc for Mass Spect* 9:866–878 (1998).

Gruić–Sovulji I. et al., Matrix–assisted laser desorption/ionisation mass spectrometry of transfer ribonucleic acids isolated from yeast, *Nucleic Acids Res.* 25(9):1859–61 (1997).

Haglund et al., Marix–assisted laser–desorption mass spectrometry of DNA using an infrared free–electron laser, *SPIE 1854*:117–128.

Henikoff, Unidirectional digestion with exonuclease III creates targeted breakpoints for DNA sequencing, *Gene* 28:351–359 (1984).

Hsiung et al., A new simpler photoaffinity analogue of peptidyl rRNA, *Nucl Acids Res* 1:1753–1762 (1974).

Hultman et al., Direct solid phase sequencing of genomic and plasmid DNA using magnetic beads as solid support, *Nucl. Acids Res.* 17:4937–4946 (1989).

Huth–Fehre et al., Matrix–assisted laser desorption mass spectrometry of oligodeoxythymidylic acids, *Rapid Comm in Mass Spect* 6:209–213 (1992).

Jacobson, et al. Applications of mass spectrometry to DNA sequencing, *GATA* 8:223–229 (1991).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Juhasz et al., Applications of delayed extraction matrix–assisted laser desorption ionization time–of–flight mass spectrometry to oligonucleotide analysis, *Analy Chem* 68:941–946 (1996).

Jurinke et al., Analysis of ligase chain reaction products via matrix–assisted laser desorption/ionization time–of–flight–mass spectrometry, *Analy Biochem* 237:174–181 (1996).

Jurinke et al., Application of nested PCR and mass spectrometry for DNA–based virus detection: HBV–DNA detected in the majority of isolated anti–HBc positive sera, *Genetic Analysis* 14:97–102 (1998).

Jurinke et al., Detection of hepatitis B virus DNA in serum samples via nested PCR and MALDI–TOF mass spectrometry, *Genetic Analysis* 13:67–71 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Kirpekar et al., DNA sequence analysis by MALDI mass spectrometry, *Nucleic Acids Res.* 26:2554–9 (1998).

Köster et al., A strategy for rapid and efficient DNA sequencing by mass spectrometry, *Nature Biotech* 14:1123–1128 (1996).

Köster et al., N–ACYL proecting groups for deoxynucleosides, A quantitative and comparative study, *Tetrahedron* 37:363–369 (1981).

Köster et al., Oligonucleotide synthesis and multiplex DNA sequencing using chemiluminescent detection, *Nucl Acids Res* 24:318–321 (1991).

Köster et al., Polymer support oligonucleotide synthesis—XV[1,2], *Tetrahedron* 40:102–112 (1984).

Köster et al., Some improvements in the synthesis of DNA of biological interest, *Nucl Acids Res* 7:39–56 (1980).

Köster et al., Well–defined insoluble primers for the enzymatic synthesis of oligo– and polynucleotides, *Hoppe–Seyler's Z. Physiol. Chem.* 359:11579–1589 (1978).

Lawrance et al., Megabase–scale mapping of the HLA gene complex by pulsed field gel electrophoresis, *Science* 235:1387–1389 (1987).

Li et al., High–Resolution MALDI Fourier Transform Mass Spectrometry of Oligonucleotides, *Anal Chem* 68:2090–2096 (1996).

Little et al., Detection of RET proto–oncogene codon 634 mutations using mass spectrometry, *J. Mol Med.* 75:745–750 (1997).

Little et al., Direct detection of synthetic and biologically generated double–stranded DNA by MALDI–TOF MS, *J. Mass Spec* 17:1–8 (1997).

Little et al., Identification of apolipoprotein E polymorphisms using temperature cycled primer oligo base extension and mass spectrometry, *Short Communiation.*

Little et al., MALDI on a chip: analysis of arrays of low–femtomole to subfemtomole quantities of synthetic oligonucleotides and DNA diagnostic products dispensed by a piezoelectric pipet, *Anal Chem* 69:4540–4546 (1997).

Little et al., Mass spectrometry from miniaturized arrays for full comparative DNA analysis, *Nature Med* 3:1413–1416 (1997).

Little et al., Verification of 50– to 100–mer DNA and RNA sequences with high–resolution mass spectrometry, *Proc. Natl. Acad. Sci. USA* 92:2318–2322 (1995).

*Methods in Enzymology,* Recombinant DNA, vol. 101, Wu, Grossman, Moldave, Eds., Academic Press, Inc., 1983.

*Methods in Enzymology,* Recombinant DNA, vol. 153, Wu, Grossman, Eds., Academic Press, Inc.

*Methods in Enzymology,* Recombinant DNA, vol. 154, Wu, Grossman, Eds., Academic Press, Inc.

*Methods in Enzymology,* Recombinant DNA, vol. 155, Wu, Ed., Academic Press, Inc.

*Methods in Enzymology,* Guide to Molecular Cloning Techniques, vol. 152, Berger, Ed., Academic Press, Inc. (1987).

*Molecular Cloning: A laboratory manual,* 2nd, ed., Ch. 11: Synthetic oligonucleotide probes, Sambrook, Cold Spring Harbor Laboratory Press New York, pp. 11.1–11.61 (1989).

Monforte and Becker, High–throughput DNA analysis by time–of–flight mass spectrometry, *Nature Medicine* 3:360–362 (1997).

Mosca et al., Mass spectrometry and DNA analysis, *Hemoglobin* 17(3):261–268 (1993).

Nielsen, et al., Sequence–Selective Recognition of DNA by Strand Displacement with a Thymine–Substituted Polyamide, *Science:*254:1497–1500 (1991).

Nordhoff et al., Ion stability of nucleic acids in infrared matrix–assisted laser desorption/ionization mass spectrometry, *Nuc Acids Res.* 21:3347–3357 (1993).

Oberbaumer, New pUC–derived expression vectors for rapid construction of cDNA libraries, *Gene* 49:81–91 (1986).

O'Donnell et al., High–density, covalent attachment of DNA to siliocn wafers for analysis by MALDI–TOF mass spectrometry, *Analytical Chemistry* 69:2438–2443 (1997).

O'Donnell et al., MassArray as an enabling technology for the industrial–scale analysis of DNA, *Genetic Engineering News* 17 (1997).

O'Donnell–Maloney et al., Microfabrication and array technologies for DNA sequencing and diagnostics, *Genetic Analysis: Biomolecular Engineering* 13:151–157 (1996).

*Organic Charge–Transfer Complexes,* R. Foster, Academic Press, Inc. (1969).

Pieles et al., Matrix–assisted laser desorption ionization time–of–flight mass spectrometry: a powerful tool for the mass and sequence analysis of natural and modified oligonucleotides, *Nucleic Acids Res.* 21:3191–3196 (1993).

Pomerantz et al., Determination of oligonucleotide composition from mass spectrometrically measured molecular weight, *Am. Soc. Mass Spectrom.* 4:204–09 (1993).

Prome et al., Use of combined mass spectrometry methods for the characterization of a new variant of human hemoglobin: The double mutant hemoglobin villeparisis beta 77(EF1), *J. American Society for Mass Spect* 7(2):163–167 (1996).

Sanger et al., DNA sequencing with chain–terminating inhibitors, *Proc. Natl. Acad. Sci.* 74P5463–67 (1977).

Schram, Mass spectrometry of nucleic acid componenents, *Biomed. App. Mass Spectrom.* 34:203–287 (1990).

Shaler et al., Effect of Impurities on the matrix–assisted laser desorption mass spectra of single–stranded oligodeoxynucleotides, *Anal. Chem.* 68:576–579 (1996).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Siuzdak, The emergence of mass spectrometry in biochemical research, *Proc. Natl. Acad. Sci. USA* 91:11290–11297 (1994).

Smith et al., New Developments in Biochemical Mass Spectrometry: Electrospray Ionization, *Anal. Chem.* 62:882–899 (1990).

Smith et al., Capillary zone electrophoresis–mass spectrometry using an electrospray ionization interface, *Anal. Chem.* 60:436–441 (1988).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Stults and Marsters, "Improved electrospray ionization of synthetic oligodeoxynucleotides", *Rapid Comm. Mass Spectrom.* 5:359–363 (1991).

Tang, et al., Improving mass resolution in MALDI/TOF analysis of DNA.

Tang et al., Matrix–assisted laser desorption/ionization mass spectrometry of immobilized duplex DNA probes, *Nucleic Acids Research* 23:3126–3131 (1995).

Valaskovic, et al., Attomole–sensitivity electrospray source for large–molecule mass spectrometry, *Anal. Chem.* 67:3802–3805 (1995).

Vorm et al., Improved resolution and very high sensitivity in MALDI TOF of matrix surfaces made by fast evaportion, *Anal. Chem.* 66:3281–3287 (1994).

Walker, et al., Multiplex strand displacement amplification (SDA) and detection of DNA sequences from *Mycobacterium tuberculosis* and other mycobacteria, *Nucleic Acids Research* 22(13):2670–2677 (1994).

Wentrup, *Reactive Molecules,* John Wiley & Sons (1984).

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yamashita et al., Electrospray ion source. Another variation on the free–jet theme, *J. Phys. Chem.* 88:4451–4459, (1984).

Berenkamp et al., "Infrared MALDI Mass Spectrometry of large Nucleic Acids" *Science* 281:260–262 (1998).

Frank and Köster, DNA chain length and the influence of base composition on electrophoretic mobility of oligodeoxyribonucleotides in polyacrylamide–gels, *Nucl. Acids Res.* 6:2069–2087 (1979).

Hillenkamp et al., "Matrix Assisted UV_Laser Desorption/ionization: A New Approach to Mass Spectrometry of Large Biomolecules", *Bio Mass Spectr.,* Burlingame and McCloskey (eds.), pp. 49–61, Elsevier Science Publishers B.V., Amsterdman (1989).

Hillenkamp and Ehring, "Laser desorption mass spectrometry Part 1: Basic mechanisms and techniques", *Mass Spectrometry in the Biological Sciences: A tutorial,* pp. 165–179 (1992).

Nordhoff, E., "Matrix–assisted laser desorption/ionization mass spectrometry of nucleic acids with wavelengths in the ultraviolet and infrared", *Rapid Comm. in Mass. Spec.* 6:771–776 (1992).

Overberg et al., "Laser Desorption Mass Spectrometry. Part II Performance and Applications of Matrix–Assisted Laser Desorption/Ionization of Large Biomolecules", *Mass Spect in the Biolog Science: A Tutorial 181–197* (1992).

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Advances the Industrial Genomics Revolution with the Launch of Its DNA MassArray™Automated Process Line, Press Release: Sep. 28, 1998, http://www.sequenom.com/pressrelease.htm.

Sequenom Reports On Use of Its DNA MassArray™Technology to Analyze Genes Associated with Alzheimer's Disease adn Arteriosclerosis: Technology Has Applications in Drug Development, Press Release: Sep. 22, 1997, http://www.sequenom.com/pressrelease.htm.

Sequenom Uses DNA MassArray™to Sequence Section of Human Cancer–Related p53 Gene, Press Release: Mar. 27, 1998, http://www.sequenom.com/pressrelease.htm.

Siegert et al. "Matrix–assisted laser desorption/ionization time–of–flight mass spectrometry for the detection of polymerase chain reaction products containing 7–deazapurine moieties" *Anal. Biochem.* 243:55–65 (1996).

Ruppert, A., Szalay, B., Horst, G. and Köster, H., Abstract for "Preparation of Plasmid DNA as Sequencing Templates in a Microtiter Plate Format", Presented at Cold Spring Harbor Laboratory, Cold Spring Harbor, NY, U.S.A., May 10–May 15, 1995.

Ruppert, A., Szalay, B., Horst, G. and Köster, H., Abstract for "A Rapid and High Throughput Method for Plasmid Isolations", Presented at Hinxton Hall, England, Aug. 31–Sep. 2, 1994; and.

Ruppert, A., Szalay, B., Horst, G. and Köster, H., Abstract for "A Rapid and High Throughput Method for Plasmid Isolations", Presented at Rauischholzhausen, Germany, Sep. 28–Oct. 1, 1994).

FILTRATION PROCESSES, KITS AND DEVICES FOR ISOLATING PLASMIDS

BACKGROUND OF THE INVENTION

Bacterial plasmids are double-stranded closed circular DNA molecules that range in size from 1 kb to more than 200 kb. They are found in a variety of bacterial species, where they behave as accessory genetic units that replicate and are inherited independently of the bacterial chromosome. Nevertheless, they rely on enzymes and proteins encoded by the host for their replication and transcription. Frequently, plasmids contain genes coding for enzymes that under certain circumstances in nature are advantageous to the bacterial host. Among the phenotypes conferred by plasmids are resistance to antibiotics; production of colicins and enterotoxins; and restriction and modification enzymes.

Plasmids are useful tools in genetic engineering. They can be joined with fragments of foreign DNA in vitro to form chimeras that can be introduced into bacterial host cells; amplified and isolated or expressed (See for example, U.S. Pat. Nos. 4,237,234; 4,740,470 and 4,468,464 to Cohen et al.). A variety of plasmids have been developed to perform specialized functions. For example, plasmids have been constructed with powerful promoters to generate large amounts of mRNA complementary to cloned sequences of foreign DNA and thereby express high levels of protein.

Various plasmids (e.g. pUC), cosmids and phagemids (e.g. pEMBL, pGEMA) are useful cloning vectors for initiating large scale sequencing projects (T. Maniatis, E. F. Fritsch and J. Sambrook (1982) Molecular Cloning. A Laboratory Manual. Cold Spring Harbor Laboratory, Cold Spring Harbor, N.Y.; *Methods in Enzymology*, Vol. 101 (1983), Recombinant DNA, Part C; Vol. 153 (1987), Recombinant DNA, Part D; Vol. 154 (1987), Recombinant DNA, Part E; Vol. 155 (1987), Recombinant DNA, Part F and Vol. 152 (1987), Guide to Molecular Cloning Techniques, Academic Press, New York). These vectors accomodate cDNA or genomic libraries of large DNA fragments.

However, the large DNA fragments generated typically can not be sequenced directly in one run, since Sanger sequencing chemistry only allows about 200 to 500 bases to be read at a time. As a result, long DNA fragments typically must be cut into shorter pieces which are separately sequenced. In one approach this is done in a fully random manner by using, for example, unspecific DNAse I digestion, frequently cutting restriction enzymes, or sonification, and sorting by electrophoresis on agarose gels (*Methods in Enzymology*, supra). However, this method is time-consuming and often not economical as several sequences are sequenced many times until a contiguous DNA sequence is obtained. Very often the expenditure of work to close the gaps of the total sequence is enormous.

Several strategies have been proposed for sequencing long DNA fragments in a non-random, i.e. direct, way from one end through to the other (Methods of Enzymology, supra; S. Henikoff, *Gene*, 28, 351–59 (1984); S. Henikoff, et al. U.S. Pat. No. 4,843,003; and PCT/Application WO 91/12341). However, none of these sequencing methods provide an acceptable method of sequencing megabase DNA sequences in either a timely or economical manner. The main reason is that these methods all rely on polyacrylamide gel electrophoresis (PAGE) as a central and key element of the overall process.

PCT patent application international publication number WO 94/16101 by Koster describes DNA sequencing procedures, which utilize Sanger base-specific, chain termination reactions to generate from an unknown DNA molecule, nested fragments that are analyzed by mass spectrometry to determine the sequence of the unknown DNA, PCT patent application international publication number WO 94/21822 by Koster describes sequencing techniques in which the mass of remaining nucleic acid molecules or the nucleotides sequentially cleaved by an exonuclease activity are analyzed by mass spectrometry to identify the unknown nucleic acid molecule.

Although restriction analyses provide useful information on an unknown DNA sequence, hybridization screening methods can reveal whether a particular sequence is present in an unknown DNA sequence and high throughput sequencing methods can provide the exact sequence of the unknown DNA, the potential of these methodologies have not as yet been realized. One problem is that existing procedures for isolating plasmids from bacterial cells are hampered by centrifugation steps and the processing of single reaction tubes. Centrifugation, which is used to collect cells, remove cellular debris and yield the DNA by ethanol precipitation, can be done simultaneously only with a small number of samples. The handling of single reaction tubes is time-consuming and bears the risk of misplacing samples. To circumvent these problems, methods for the purification of bacteriophage M13 sequencing templates in 96-well microtiter (mt) plates have been developed (Smith, V. et al., (1990) *DNA Sequence* 1, 73–78; and Alderton, R. P. et al., (1992) *Anal. Biochem.* 201, 166–169). Microtiter filter plates have also been employed for harvesting M13 from culture supernatants (Eperon, I. C. (1986) *Anal. Biochem.* 156, 406–412).

A means to rapidly isolate large numbers of plasmid DNA from plasmid containing cells is needed, particularly for screening large numbers of clones (e.g. for mutations), performing restriction analyses or for performing high throughput DNA sequencing.

SUMMARY OF THE INVENTION

In general, the instant invention provides processes, kits and preferred devices for rapidly isolating large numbers of plasmid DNAs from plasmid containing cells. Once obtained, the isolated plasmid DNA can be analyzed by hybridization screening or restriction analysis. Alternatively the plasmid DNA can be sequenced.

In one aspect, the invention features a process for isolating plasmid DNAs from plasmid containing cells by: a) filtering plasmid containing cells with a wash solution to disrupt the cell membrane and degrade RNA; b) incubating the plasmid containing cells with a lysis/denaturation solution to lyse the bacterial cells and denature nucleic acids; c) incubating the product of claim b with a renaturation solution for an appropriate period of time and at an appropriate temperature to yield a mixture containing dissolved plasmid DNA, insoluble clots of linear DNA and cellular debris; d) filtering the product of step c) to capture clots of linear DNA and cellular debris on a filter; and e) obtaining plasmid DNA from the filtrate. Preferably, plasmid DNA is obtained from the filtrate by precipitation and capture onto a filter. In addition, preferably the filtration steps are performed under vacuum or high pressure. Most preferably, the process is performed in a plurality of microtiter wells, which are in contact with a regulatable vacuum or pressure source. By performing the process in a microtiter plate arrangement, a number of different plasmid containing cell cultures can be processed simultaneously. Another advantage of a microtiter plate arrangement is that plasmid containing cells can be grown in the microtiter wells and directly processed.

In another aspect, the invention features high throughput DNA sequencing methods. In one embodiment, the method comprises the steps of: a) cloning an unknown DNA sequence into a plasmid; b) filtering plasmid containing cells with a wash solution to disrupt the cell membrane and degrade RNA; c) incubating the plasmid containing cells with a lysis/denaturation solution to lyse the bacterial cells and denature linear DNA; d) renaturing the DNA to yield a mixture containing plasmid DNA, insoluble clots of linear DNA and cellular debris; e) filtering the product of step d) to capture cellular debris and the insoluble clots of linear DNA on a filter; f) obtaining plasmid DNA from the filtrate; and g) analyzing the plasmid DNA or nucleic acid fragments obtained from the plasmid DNA by mass spectrometry to determine the unknown DNA sequence.

In a third aspect, the invention features kits for rapidly isolating large numbers of plasmids, for example for use in performing a high throughput DNA sequencing, restriction analysis or hybridization screening.

In a final aspect, the invention features preferred filtration devices comprised of multiwell, microtitre filter plates. Preferably the devices permit the retention of liquid in the wells during the desired incubation period followed by removal of the liquid from each well by filtration, preferably in association with a vacuum or pressure source. Also, preferably, the device permits the analysis of filtrate without cross contamination between wells.

The instant invention allows simultaneous isolation of a large number of different plasmids. A key advantage of this procedure over prior art plasmid preparation procedures is the replacement of all centrifugation steps by filtration. The above and further features and advantages of the instant invention will become clearer from the following Detailed Description and Claims.

DETAILED DESCRIPTION OF THE INVENTION

The invention features processes, kits and preferred devices for rapidly isolating plasmid DNA from plasmid containing cells. As used herein, the term "plasmid" refers to closed circular DNA molecules (single or double stranded) that are maintained in a host cell separate from the host cell genome. The term encompasses naturally occuring bacterial plasmids and derivatives thereof, recombinant plasmids, genetically engineered cosmids and episomes in prokaryotic or eukaryotic host cells.

In general, the novel process for isolating plasmid DNAs from plasmid containing cells involves the following steps: a) filtering plasmid containing cells with a wash solution to disrupt the cell membrane and degrade RNA; b) incubating the plasmid containing cells with a lysis/denaturation solution to lyse the bacterial cells and denature nucleic acids; c) incubating the product of step b with a renaturation solution for an appropriate period of time and at an appropriate temperature to yield a mixture containing dissolved plasmid DNA, insoluble clots of linear DNA and cellular debris; d) filtering the product of step c) to capture clots of linear DNA and cellular debris on a filter; and e) obtaining plasmid DNA from the filtrate.

One advantage provided by the instant process is that plasmid containing cells can be grown directly in the wells of a microtiter plate. In general, a sufficient plasmid yield for screening large numbers of clones or for use in high throughput DNA sequencing can be obtained from about $10^8$–$10^9$ cells grown in appropriate growth medium, overnight at room temperature in a 0.25–1 mL well.

Figure 1:
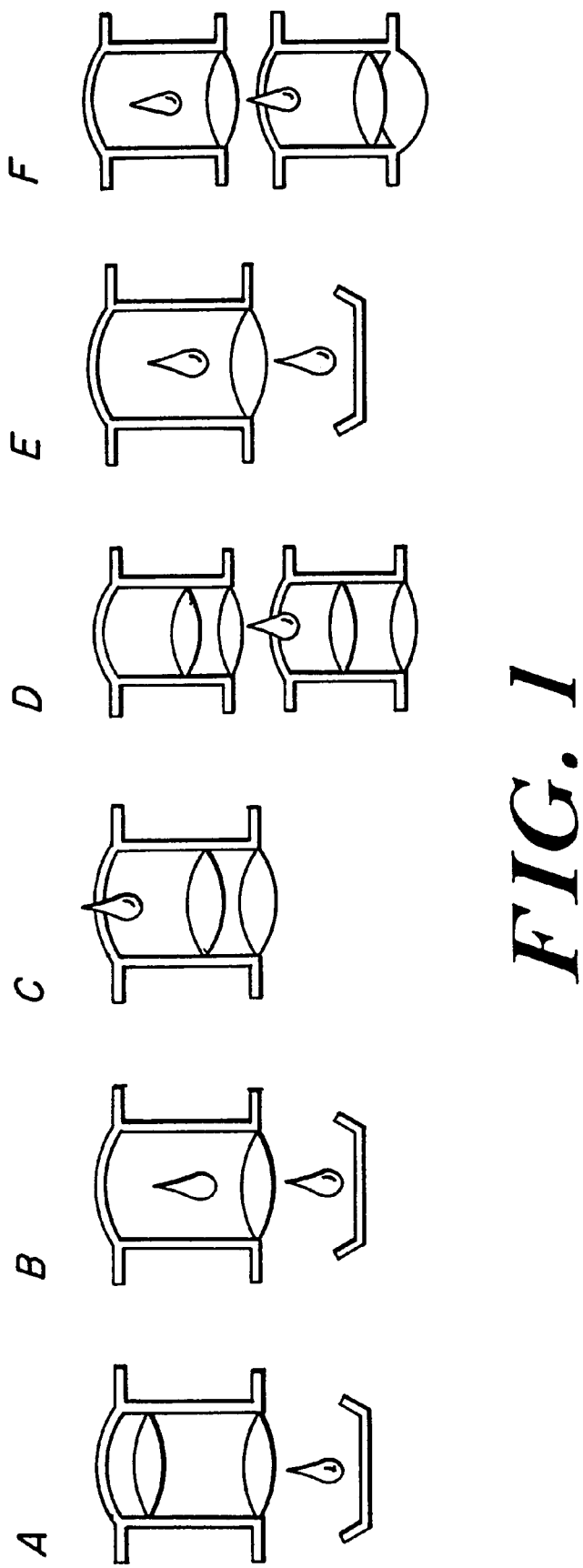
FIG. 1 is a schematic representation of a filtration process for plasmid isolation. A) 0.35 ml of a stationary overnight culture are filled into each well of the microtiter (mt) filter plate. Culture medium is removed by suction into a waste tray under the mt filter plate. By repeating this step about 0.8 ml. overnight culture could be collected and filtrated per well. B) 0.1 ml of a wash solution are used to wash the pellet. C) The pellet is agitated and incubated with 0.1 ml of a lysis solution for about 5 minutes. After the addition of 0.075 of a salt solution, the mt filter plate is agitated and cooled for about 30 minutes. D) The supernatant is filtrated into another mt filter plate positioned under the first one to collect the clear filtrate. Due to the presence of an alcohol in the wells of the lower positioned filter plate, the plasmid DNA is precipitated. E) The precipitated DNA is washed and the filtrates collected in a waste tray. F) The plasmid DNA on the filter is dried at room temperature for at least 5 minutes, dissolved in 0.1 ml water and transferred by suction into a standard U-shaped mt plate and either processed for restriction and/or sequencing or covered with a plastic wrap and stored in a freezer.
Figure 2:
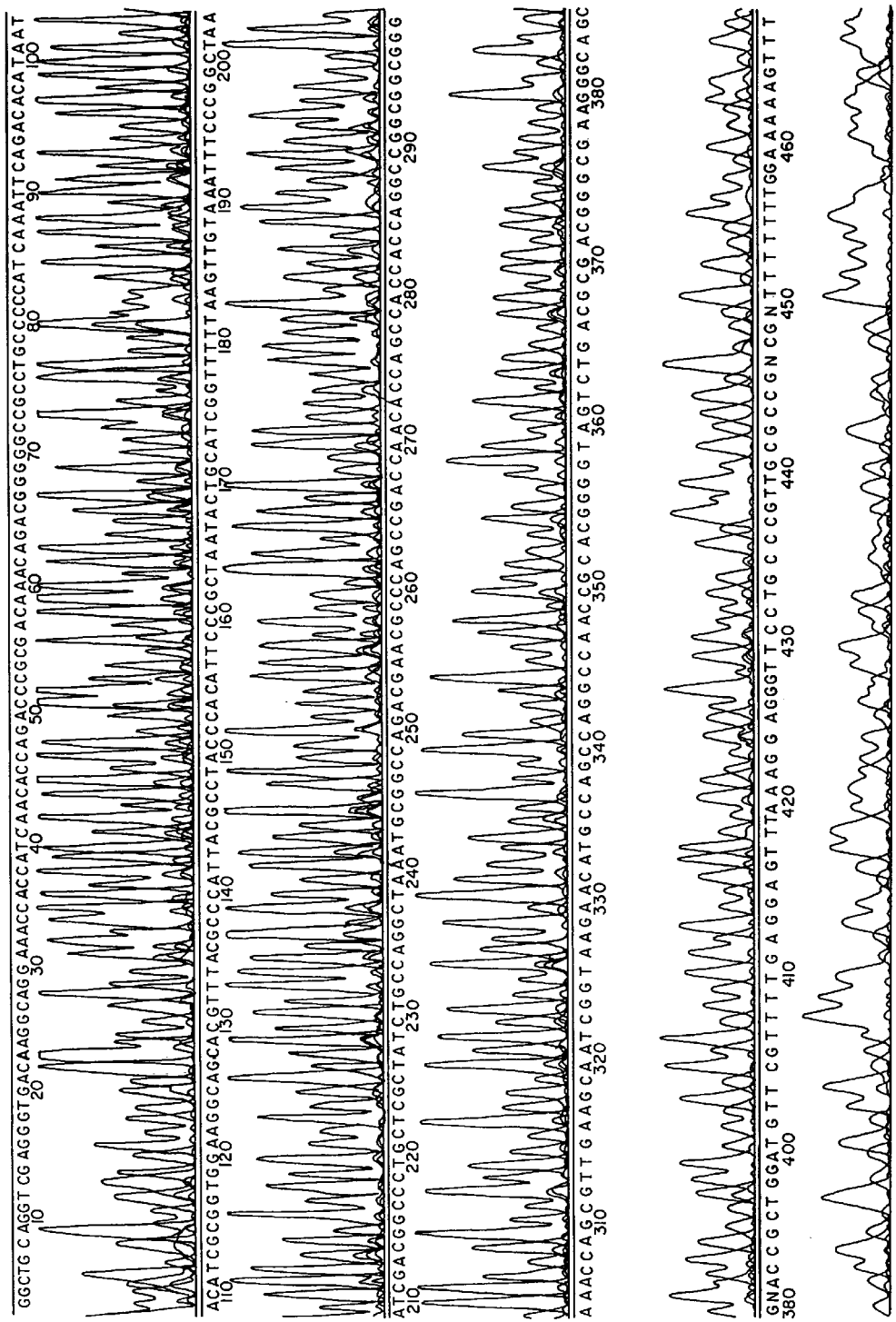
FIG. 2 is a read out of the amount of DNA (pOM8 derivative) obtained in one well with the ReadyReaction DyePrimer (−21m13) Cycle Sequencing Kit on an ABI 373A DNA Sequencer (Applied Biosystems).

Cells present in each well are then washed and filtered, preferably in a pressure chamber or vacuum, to disrupt cell membranes and degrade RNA (See FIG. 1). A particularly useful wash solution contains an isotonic buffer (e.g. a Tris buffer; or a sucrose or glucose solution), a chelating agent (e.g. ethylenediaminetetraacetic acid (EDTA) or (CDTA)) and an RNAse (e.g. RNAse A, RNAse B, RNAse C, RNAse N1, RNAse T1, RNAse U1 or RNAse U2). The wash solution may also optionally include lysozyme to further weaken cell walls, particularly if large plasmids (e.g. greater than about 45 kb) are being isolated.

After the wash and filtration step, cells are lysed and linear DNA is denatured, preferably by incubation in an alkaline lysis solution at an appropriate temperature and for an appropriate period of time. As shown in the following example, thorough lysis and denaturation can be accomplished by incubating cells in a sodium hydroxide, sodium dodecyl sulfate solution for about 5 to 10 minutes at room temperature. Optionally, more reactive reagents, such as phenol and chloroform (equal volumes) may be included in the lysis/denaturation solution.

A third, renaturation solution is then added and incubated to yield a mixture containing plasmid DNA, insoluble clots of linear DNA and cellular debris. A preferred process involves agitating the lysate in (e.g. KOAc, pH 4.8 and NaCl) and storing the mixture for at least about 25–30 minutes, preferably at a cold temperature (e.g. at least at about −15° C.) For example, storage can occur in a freezer set at −20° C. or in ice, in which case the filter bottom may be covered, e.g. with aluminum foil.

Clots of linear DNA and cell debris can then be removed by filtration and the clear filtrate containing dissolved plasmid DNA transferred to a second microtiter filter plate prefilled with a solution (e.g. an alcohol) to precipitate the plasmid DNA. This second plate is preferably positioned directly under the first plate.

The filtrate containing the plasmid DNA can then be analyzed or the DNA can optionally be dried and then redissolved (e.g. in water) or stored preferably in a freezer at about −20° C.

In another aspect, the invention features processes for generating samples to be analyzed by a high throughput DNA sequencing method, such as mass spectrometry, preferably using matrix-assisted, laser desorption/ionization—time of flight (MALDI-TOF) or a MALDI-FT format. In one embodiment, the process comprises the steps of: a) cloning an unknown DNA sequence into a plasmid; b) filtering plasmid containing cells with a wash solution to disrupt the cell membrane and degrade RNA; c) incubating the plasmid containing cells with a lysis/denaturation solution to lyse the bacterial cells and denature linear DNA; d) renaturing the DNA to yield a mixture containing plasmid DNA, insoluble clots of linear DNA and cellular debris; e) filtering the product of step d) to capture cellular debris and the insoluble clots of linear DNA on a filter; f) obtaining plasmid DNA from the filtrate; and g) analyzing, the plasmid DNA or nucleic acid fragments obtained from the plasmid DNA by mass spectrometry to determine the unknown DNA sequence.

Preferred procedures for performing mass spectrometry analyses of nucleic acid fragments are described in PCT patent application international publication number WO 94/16101 by Köster and PCT patent application international publication number WO 94/21822 also by Köster which are flly incorporated by reference herein.

To facilitate mass spectrometric analysis, base specifically terminated fragments can be immobilized or attached to a solid support, such as a filter membrane or a sidewell of the microtiter plate. Such attachment can be accomplished, for example, by hybridization of the universal primer sequence to a complementary sequence covalently linked to the membrane or by a linking functionality on the universal primer which interacts with a functional group on the membrane to form a linkage which is reversible under chemical, enzymatic or physical conditions (i.e. is cleaved during mass spectrometry).

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected. So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., Science, 254, 1497 (1991)) which render the base sequence less susceptible to enzymatic degradation and hence increases overall stability of the solid support-bound capture base sequence.

Alternatively, a target detection site can be directly linked to a solid support via a reversible or irreversible bond between an appropriate functionality (L') on the target nucleic acid molecule (T) and an appropriate functionality (L) on the capture molecule. A reversible linkage can be such that it is cleaved under the conditions of mass spectrometry (i.e., a photocleavable bond such as a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

By way of example, the L-L' chemistry can be of a type of disulfide bond (chemically cleavable, for example, by mercaptoethanol or dithioerythrol), a biotin/streptavidin system, a heterobifunctional derivative of a trityl ether group (Köster et al., "A Versatile Acid-Labile Linker for Modification of Synthetic Biomolecules," *Tetrahedron Letters* 31, 7095 (1990)) which can be cleaved under mildly acidic conditions as well as under conditions of mass spectrometry, a levulinyl group cleavable under almost neutral conditions with a hydrazinium/acetate buffer, an arginine—arginine or lysine—lysine bond cleavable by an endopeptidase enzyme like trypsin or a pyrophosphate bond cleavable by a pyrophosphatase.

The functionalities, L and L,' can also form a charge transfer complex and thereby form the temporary L-L' linkage. Since in many cases the "charge-transfer band" can be determined by UV/vis spectrometry (see e.g. *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g. *Reactive Molecules* by C. Wentrup, John Wiley & Sons, 1984).

An anchoring function L' can also be incorporated into a target capturing sequence by using appropriate primers during an amplification procedure as described further below.

Prior to mass spectrometric analysis, it may be useful to "condition" nucleic acid molecules, for example to decrease the laser energy required for volatization and/or to minimize fragmentation. Conditioning is preferably performed while a nucleic acid fragment is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as akyliodide, iodoacetamide, β-iodoethanol, or 2,3-epoxy-1-propanol, the monothio phosphodiester bonds of a nucleic acid molecule can be transformed into a phosphotriester bond. Further conditioning involves incorporating nucleotides which reduce sensitivity for depurination (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

Prior to analysis by mass spectrometry, the nucleic acid fragments can be amplified to generate an appropriate quantity of a nucleic acid molecules on which to perform mass spectrometry. Examples of appropriate amplification procedures for use in the invention include: cloning (Sambrook et al., Molecular Cloning: A Laboratory Manual, Cold Spring Harbor Laboratory Press, 1989), polymerase chain reaction (PCR) (C. R. Newton and A. Graham, PCR, BIOS Publishers, 1994), ligase chain reaction (LCR) (F. Barany Proc. Natl. Acad. Sci USA 88, 189–93 (1991), strand displacement amplification (SDA) (G. Terrance Walker et al., Nucleic Acids Res. 22, 2670–77 (1994)) and variations such as RT-PCR, allele-specific amplification (ASA) etc.

In a further aspect, the invention features kits for performing plasmid filtrations. For example, in one embodiment, the kit comprises: 1) a container of a cell growth medium; 2) a container of a cell wash solution; 3) a container of lysis/denaturation solution; 4) a container of renaturation solution; and 5) a container of a solution for precipitating DNA.

The kit can also optionally include containers of reagents for performing further reactions on the isolated plasmid DNA. For example, the kit can include containers of restriction enzymes; DNA polymerases (e.g. DNA polymerase I (Holoenzyme), large fragment of DNA polymerase I (Klenow fragment), bacteriophage $T_4$ DNA polymerase, bacteriophage $T_7$ DNA polymerase, modified bacteriophage $T_7$ DNA polymerase, Taq DNA polymerase, reverse transcriptase (RNA-dependent and DNA-dependent) and terminal transferases); DNA-dependent DNA polymerase (bacteriophage SP6 and bacteriophage T7 and T3 RNA polymerase); ligases (bacteriophage $T_4$ DNA ligase, E. coli DNA ligase, bacteriophage $T_4$ RNA ligase); kinases; methylases; phosphatases (e.g. alkaline phosphatase); and nucleases (e.g. nuclease BAL, nuclease S1, mung-bean nuclease, ribonucleases (RNAse A, RNAse B, RNAse C, RNAse N1, RNAse T1, RNAse U1 or RNAse U2), exonuclease III, bacteriophage λ exonuclease.

In another aspect the invention comprises a preferred filtration device comprising a multiwell microtiter filter plate. The wells must be of an appropriate volune to accommodate an appropriate number of plasmid containing cells to yield sufficient plasmid DNA. However, too large a volume comprising too many plasmid containing cells can result in membrane clogging in any of the subsequent filtration steps.

Preferably, the membrane has an appropriate pore diameter for retaining plasmid DNA (e.g. 0.1–1 μm), but not other cell components. Representative suitable microporous membranes include nitrocellulose, cellulose, cellulose acetate, polycarbonate, polyvinylidene fluoride, polysulfone. The use of composite, multilayered membranes including glass fiber can also be envisioned. The filter membrane can also be functionalized by the introduction of groups such as amino, hydroxy, thio, carboxy, activated carboxy groups The precipitated DNA is dissolved in an aqueous solution (e.g. water or an aqueous buffer) and transferred by suction (or pressure) into a standard microtitre plate (e.g. with a U-shaped bottom).

Figure 3:
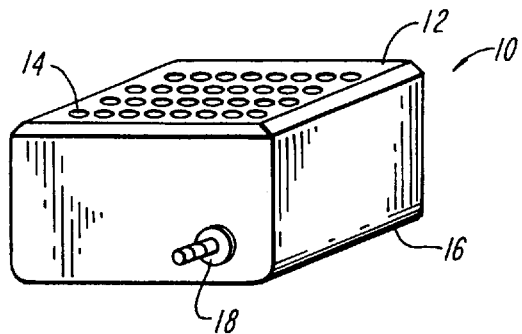
FIG. 3 is a planar view of a filtration apparatus.

FIG. 3 illustrates one filtration apparatus 10 suitable for use in the above-described filtration process. The illustrated filtration apparatus 10 incudes a multi-well plate 12 having a plurality of individual well elements 14. The plate 12 sits above a base element 16 that includes a vacuum connector 18 for connecting to a pump element. The plate 12 is removably and replaceby mounted to the base 16 so that, as will be described in greater detail hereinafter, the plate 12 can be seated above a lower plate of plural wells or a waste tray, and filtrate from the first plate 12 can pass to the wells of the lower plate or into the waste tray.

Figure 4:
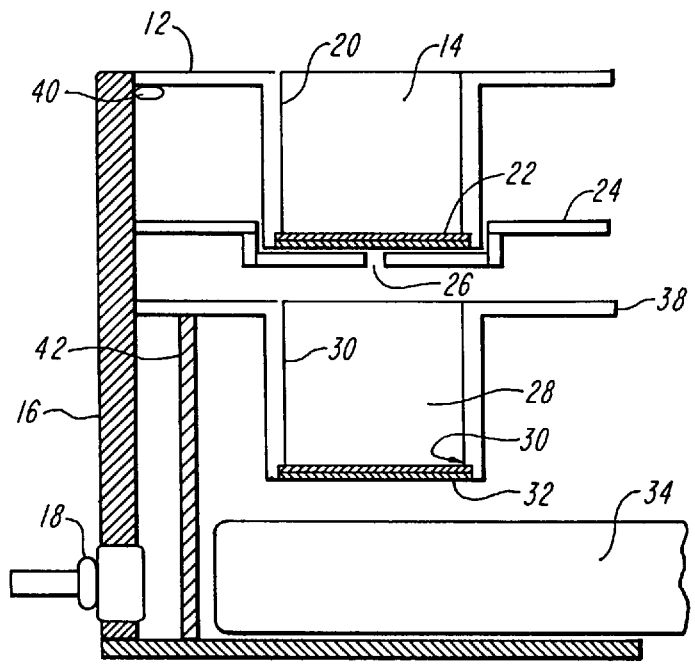
FIG. 4 is a cross-sectional view of the apparatus depicted in FIG. 3.

FIG. 4 illustrates a cross-sectional view of the filter apparatus 10 depicted in FIG. 3 with the filter plate 12 seated against the gasket element 40 that extends around the inner sidewall of the base 16. FIG. 4 illustrates that the filter apparatus 10 can include a multi-well plate 12 that has a plurality of well elements 14, each of which includes a sidewall 20 having a filter membrane 22 that spans across a lower portion of the well element 14. Optionally, the base 16 includes a support plate 24 disposed below the filter membrane 22 and adapted to collect filtrate passing through the membrane 22. To this end, the support plate 24 includes a central aperture 26 adapted to allow filtrate to flow from the individual wells 14 and to direct the droplets of filtrate into a container disposed beneath the plate 12. As further depicted by FIG. 4, the illustrated filter apparatus 10 includes a base element 16 that has a support post 42 that can hold a lower plate 38 that has a plurality of individual well elements 28, each of which is disposed beneath a well element 14 of the multi-well plate 12. The illustrated lower plate 38 is removably and replaceably mounted onto the post 42. Each lower well element 28 includes a sidewall 30 and a filter element 32 that spans across the lower portion of the sidewall 30. As further illustrated by FIG. 4, a waste tray element 34 can be disposed along the bottom wall of the base 16. In typical practice of the invetion, either the waste tray 34 or the lower plate 38 would be disposed beneath the plate element 12 to collect the filtrate passing therefrom.

As further depicted by FIG. 4, the plate element 12 sits above a gasket ring 40 that extends around the interior periphery of base element 16 and forms a shelf for receiving the plate element 12. The plate element 12 can sit against the gasket 40 for forming an airtight seal upon the evacuation of air from the base element 16 through the vacuum port 18.

Figure 5:
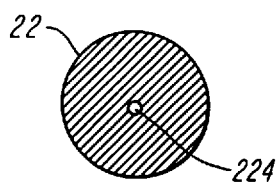
FIG. 5 is a detailed view of the filter element 22 shown in FIGS. 3 and 4.

FIG. 5 illustrates in more detail one filter element 22 which can be a two-ply membrane sealed at its periphery to the sidewall 20. The top ply of membrane 22 can be of polyvinylidene fluoride (PVDF) with a port diameter of 0.2 μm with low binding capacity for nucleic acids and proteins. The bottom ply of filter element 22 can optionally be formed by an impermeable fluoropolymer with a central hole 22a that improves dripping properties. This filter membrane 22 is preferably adapted to be tight under pressures within the filter apparatus 10, but allows controlled dropwise filtration when a vacuum is applied through port 18. In such conditions, the gasket element 40, as well as the filter elements 22 or 32, cooperate to maintain a vacuum pressure within the filter apparatus 10. Optionally, a fluid, such as water, can be added to any wells that are not employed for receiving a sample, such that a low pressure is more easily maintained within the filter apparatus 10.

As described above, in operation plasmid containing cells are placed into one or more of the wells 14 and are washed to disrupt cell membranes and degrade RNA. By application of a vacuum through port 18 a pressure is generated within the apparatus 10 and filtrate material is drawn through the filter element 22. The waste tray is positioned directly below the plate element 12 to collect the filitrate and the filtrate is discarded and the cellular material is maintained within the well 14. After the wash and filtration step, cells within well 14 are lysed by incubation in a lysis solution. An ice-cold isotonic solution is then added to the lysate and agitated and stored for the appropriate time at the appropriate temperature. The denatured proteins and cell debris are then removed by filtration, preferably by vacuum, the lower plate 38 is disposed beneath the plate element 12 and the clear filtrate is transferred to the lower wells 28 which are then prefilled with alcohol. The precipitated DNA is then optionally agitated and filtered and washed with a cold alcohol solution. The filtrate containing the plasmid DNA can then be analyzed. Optionally, the plate 12 and the plate 38 are interchangeable so that during these optional steps, the plate element 12 can be removed from the base 16 and the lower plate 38 can be seated against the gasket 40 to form a pressure seal with the base 16. Waste filtrate can be collected from the plate 38 and into the tray 34 by application of a vacuum.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLES

Comparison of Yield and Purity of Plasmid DNA Isolated by: 1) Filtration, 2) Alkaline Lysis or 3) a Qiagen Midi Column Materials and Methods Bacterial Strains and Plasmids E. coli K12 strains HB101 and XL1-Blue (Stratagene) were grown in LB broth (Miller, J. (1972) Experiments in Molecular Genetics, Cold Spring Harbor Laboratory, Cold Spring Harbor, N.Y.) supplemented with 100 μg ampicillin/mL (Binotal, Bayer). Plasmids were multicopy derivatives from pOM8 and pOM9 (Oberbäumer, I. (1986) Gene 49, 81–91): pOM8BAP2 carries a 2444-bp RsaI-XhoI fragment with the phoA gene of E. coli (Chang, C. N., Kuang, W. J., and Chen, E. Y. (1986) Gene 44, 121–125) between the SmaI and SalI restriction site of pOM8. Clones 2C–2G and 3C–3G were XL-1-Blue cells harboring pOM9 with HindIII fragments of Thermus aquaticus (T. aquaticus) genomic DNA.

DNA Isolation

To compare purity and yield of plasmid DNA isolated via the filtration method with the frequently used alkaline lysis method (Birnboim, H. C., and Doly, J. (1979) Nucleic Acids Res. 7, 1513–1523) and the use of Qiagen midi column (Qiagen, Hilden) aliquots of the same bacterial culture were processed in parallel.

Restriction Analysis

Plasmid DNA was incubated with restriction enzymes (Boehringer, Mannheim) according to manufacturer's protocol. The digested DNA sample was mixed with 5 μL loading buffer (50 mM EDTA, 50% glycerol, 0.005% bromophenol blue) and fragments were separated by electrophoresis on a 1% agarose gel. As a length standard the DNA molecular weight standard II (Boehringer Mannheim) was used. After staining with ethidium bromide, DNA bands were visualized with a uv transilluminator at 254 nm and photographed using a Polaroid CU-5 Land camera equipped with an orange filter on a Polaroid 667 film.

Plasmid Sequencing

Sequence analysis with internal $^{35}$S label was carried out with the SequiTherm Cycle Sequencing Kit (Epicentre Technologies), 10 μCi [$^{35}$S]dATP (NEN duPont), and the M13 universal (−20) sequencing primer.

Sequencing reaction for the automated sequencing was carried out with the Ready Reaction Dye Primer Cycle Sequencing Kit and the −21M13 Dye Primer (Applied Biosystems). The sequence was developed on a Model 373A DNA sequencer (Applied Biosystems).

Plasmid Isolation by Filtration (FIG. 1)

If less than 96 samples were to be processed, the remaining wells of the mt filter plate (Eppendorf) were filled with 0.1 mL water. These wells could be reused in subsequent experiments. In each well of the mt filter plate with a maximal volume of 0.37 mL, 0.35 mL of an E. coli overnight culture (about $10^9$ cells) was filtered and washed with 0.1 mL solution I (50 mM Tris-HCl, pH8, 10 mM EDTA, 0.1 mg/ml RNase A) in the EVENT suction chambers (Eppendorf). The filtrates were collected in a waste tray in the suction chamber. By repeating this step 0.8 mL of an E. coli overnight culture could be processed in each well. Applying larger volumes resulted in clogging of the membranes in the subsequent filtration steps after alkaline lysis. In the experiments described here, only a culture volume of up to 0.35 mL per well was employed. Lysis was achieved by incubation with 0.1 mL solution II (140 mM NaOH, 0.7% SDS) for 5 min at room temperature. After addition of ice-cold 0.075 mL solution III (2.25 M KOAc, pH 4.8, 0.56 M NaCl) the microtiter plate was agitated vigorously and placed for 30 min on ice covered with aluminum foil, or stored for 30 min in a freezer at −20° C. Denatured proteins and cell debris were removed by filtration, and the clear filtrate was transferred by suction into a second mt filter plate prefilled with 0.1 mL isopropanol per well. This second mt filter plate was positioned in the chamber right underneath the first one and the waste tray was replaced. After shaking, the precipitated DNA was filtered and washed with 0.35 mL ice-cold 70% ethanol, and the filtrate was collected in the waste tray. The DNA was dried at room temperature for 5 min, dissolved in 0.1 mL water, and transferred by suction into a standard microtiter plate, preferably with U-shaped bottom. The microtiter plate with 96 or less isolated plasmid DNAs was sealed with adhesive tape and stored in a freezer at −20° C.

Plasmid DNA Yields

To ensure reproducibility of the isolation procedure, 10% aliquots (10 μL) of the pOM8BAP2 DNA solution randomly picked from different wells of one mt filter plate were loaded on a 1% agarose gel. The band intensities displayed comparable amounts of isolated plasmid DNA in each well. Due to the RNase A contents in solution 1, the RNA contamination in the samples processed by the filtration method was greatly reduced. In contrast, DNA isolated by the standard alkaline lysis procedure was contaminated with large amounts of RNA.

Both complete precipitation and retention of the precipitated plasmid DNA on the membrane filter were crucial for this isolation procedure. To detect residual plasmid DNA in the filtrate after isopropanol precipitation, filtrates from single wells were collected in a standard mt filter plate and mixed in an Eppendorf tube with 1 mL ethanol and subjected to centrifugation for 20 min at 15,000 g. The pellet was dissolved in 100 μL water and 10% was analyzed by agarose gel electrophoresis; only traces of plasmid DNA could be detected.

Regarding plasmid DNA yields, the filtration method was compared with mini preparation in Eppendorf tubes and the use of Qiagen midi columns by isolating plasmid DNA from the same bacterial overnight culture starting with volumes of 0.35, 1.5, and 50 mL, respectively. The Qiagen midi column was chosen to obtain sufficient amount of DNA for uv measurement. Since plasmid DNA isolated by the alkaline lysis method, was contaminated with proteins and residual RNA, and therefore could not be measured directly by its absorbance at 260 nm, the amount of isolated plasmid DNA was estimated by comparing band intensities on ethidium bromide stained gels according to the minigel method (Maniatis, T., Fritsch, E. F., and Sambrook, J. (1982) Molecular Cloning: A Laboratory Manual, Cold Spring Harbor Laboratory, Cold Spring Harbor, N.Y.). DNA aliquots derived from 35 µL culture (10% of total plasmid yield per well in 10 µL) were analyzed on a 1% agarose gel. The average yield with the pOM-derived multicopy plasmid was estimated to be 0.3 to 0.5 µg per well.

Restriction Analysis

Ten microliters of the isolated plasmid DNA solution (i.e., 10% of a total yield per well) of pOM8BAP2 was incubated with the restriction enzymes EcoRI, DraI, and PstI (Boehringer, Mannheim), mixed with loading buffer, and separated by agarose gel electrophoresis. The expected fragments were obtained. Degradation due to contamination with exonucleases was not observed. It is apparent that with the filtration method, no further purification step such as phenol/chloroform extraction was needed. Moreover, traces of residual RNA had no negative influence on the activity of restriction endonucleases and did interfere with the detection of smaller DNA fragments on agarose gels. An additional RNase treatment was therefore not necessary.

Bacterial Cultivation in mt Filter Plates

Another advantage of the filtration method, is that the plasmid DNA preparation process could be initiated by growing the bacterial cells directly in the wells of the Eppendorf mt filter plate. The wells were filled with 0.35 mL of LB broth supplemented with ampicillin (100 µg/mL). *E. coli* clones harboring HindIII genomic fragments from *T. aquaticus* in pOM9 vector were inoculated with tooth-picks or pipet tips directly from an agar plate. The mt filter plates were incubated overnight at 37° C. in an incubator. To avoid evaporation during incubation, the mt filter plates were placed in a plastic box containing a water reservoir. Alternatively, mt filter plates covered with a second mt filter plate filled with water were incubated overnight at 37° C. under shaking at 800 rpm on a thermomixer (Eppendorf). Both procedures worked comparably well. Plasmid DNA prepared from the clones grown in mt filter plates was found to be equal in amount and quality to the bacterial cultures grown separately in a standard incubator under shaking.

For storage 5 µL aliquots of the bacterial clones from each of the 96 wells were transferred prior to filtration with a multichannel pipet into a standard mt plate containing 100 µL medium in each well. Sealed with Saran Wrap or adhesive tape, the clones could be stored for a couple of days at 4° C.

Sequence Analysis with Internal $^{35}$S Label in the Cycle Sequencing Reaction pOM9-derived plasmids with genomic HindIII fragments from *T. aquaticus* were analyzed. Ninety percent of the total yield from clone 3A was ethanol precipitated and dissolved in 4 µL water. The reaction mix was carried out as prescribed for the Sequitherm kit (Epicentre Technologies) with the M13 universal sequencing primer. The cycle program consisted of a denaturation step of 5 min at 95° C. and 30 cycles each of 30 s at 95° C., 30s at 40° C., and 60 s at 70° C. The annealing step in the cycle (30 s at 40° C.) was important to obtain high quality sequencing results.

The total reaction mixtures were run on a sequencing gel. The X-ray film was exposed overnight. The first 100 nt of the *T. aquaticus* sequence had a GC content of 58%.

Automated Sequencing with the ABI 373A DNA Sequencer

The amount of plasmid DNA pOM8BAP2, obtained from a single well was used for DNA sequencing reactions. Following the standard protocol as described in the Ready Reaction Dye Primer Cycle Sequencing Kit (Applied Biosystems) with −21M13 Dye Primer, reliable readings up to 400 and more bases could be obtained.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A process for isolating plasmid DNA from plasmid-containing cells, comprising the steps of:
   a) washing plasmid-containing cells by filtration with a wash solution to disrupt the cell membrane and degrade RNA;
   b) incubating the resulting washed plasmid-containing cells with a lysis/denaturation solution to lyse the cells and denature DNA;
   c) incubating the product of step b) with a renaturation solution for an appropriate period of time and at an appropriate temperature to yield a renatured mixture containing dissolved plasmid DNA, insoluble linear DNA and cellular debris;
   d) filtering the product of step c) to obtain a filtrate from which insoluble linear DNA and cellular debris have been removed; and
   e) obtaining plasmid DNA from the filtrate, wherein no centrifugation step is used in the process.

2. A process of claim 1, wherein the wash solution is comprised of an isotonic buffer, a chelating agent and an RNAse.

3. A process of claim 2, wherein the isotonic buffer is selected from the group consisting of: a Tris buffer, a sucrose solution or a glucose solution.

4. A process of claim 3, wherein the chelating agent is selected from the group consisting of EDTA or CDTA.

5. A process of claim 2 wherein the RNAse is a RNAse A.

6. A process of claim 2, wherein the wash solution additionally comprises a lysozyme.

7. A process of claim 1, wherein the lysis solution is alkaline.

8. A process of claim 7, wherein the lysis solution comprises sodium hydroxide and sodium dodecyl sulfate.

9. A process of claim 7 wherein the lysis solution contains equal volumes of phenol and chloroform.

10. A process of claim 1, wherein prior to step a), plasmid containing cells are grown in wells of a multi-well filter plate.

11. The method of claim 1, wherein plasmid is obtained from the filtrate by filtering the product of step d) into a multiwell plate that is prefilled with a solution comprising an alcohol for precipitating the plasmid DNA, filtering the resulting mixture, whereby the plasmid DNA collects in the wells of the multiwell plate.

12. A process for isolating plasmid DNA from plasmid-containing cells, comprising the steps of:

a) washing plasmid-containing cells by filtration with a wash solution to disrupt the cell membrane and degrade RNA;

b) incubating the resulting washed plasmid-containing cells with a lysis/denaturation solution to lyse the cells and denature DNA;

c) incubating the product of step b) with a renaturation solution for an appropriate period of time and at an appropriate temperature to yield a renatured mixture containing dissolved plasmid DNA, insoluble linear DNA and cellular debris;

d) filtering the product of step c) to obtain a filtrate from which insoluble linear DNA and cellular debris have been removed; and e) obtaining plasmid DNA from the filtrate, wherein:
   the process is performed in a multi-well filtration device; and
   prior to step a), plasmid containing cells are grown in wells of a multi-well filter plate.

13. A process of claim 12, wherein the lysis solution is alkaline.

14. A process of claim 13, wherein the lysis solution comprises sodium hydroxide and sodium dodecyl sulfate.

15. A process of claim 13, wherein the lysis solution contains equal volumes of phenol and chloroform.

16. A high throughput DNA sequencing method, comprising the steps of:

i) growing plasmid containing cells wherein the plasmids comprise DNA to be sequenced;

ii) washing plasmid-containing cells by filtration with a wash solution to disrupt the cell membrane and degrade RNA;

iii) incubating the resulting washed plasmid containing cells with a lysis/denaturation solution to lyse the cells and denature DNA;

iv) incubating the product of step c) with a renaturation solution for an appropriate period of time and at an appropriate temperature to yield a renatured mixture containing dissolved plasmid DNA, insoluble linear DNA and cellular debris;

v) filtering the product of step d) to obtain a filtrate from which insoluble linear DNA and cellular debris have been removed;

vi) obtaining plasmid DNA from the filtrate; and vii) analyzing a nucleic acid fragment obtained from the plasmid DNA by mass spectrometry to determine the sequence of the fragment of DNA of the plasmid.

17. A process of claim 16, which is performed in a multi-well filtration device that includes a multi-well filter plate.

18. A process of claim 17, wherein prior to step b), plasmid-containing cells are grown in the wells of the multi-well filter plate.

19. A process of claim 16, wherein the wash solution is comprised of an isotonic buffer, a chelating agent and an RNAse.

20. A process of claim 19, wherein the isotonic buffer is selected from the group consisting of:
a Tris buffer, a sucrose solution or a glucose solution.

21. A process of claim 20, wherein the chelating agent is selected from the group consisting of EDTA or CDTA.

22. A process of claim 19, wherein the wash solution additionally comprises a lysozyme.

23. A process of claim 16, wherein the lysis solution is alkaline.

24. A process of claim 23, wherein the lysis solution comprises sodium hydroxide and sodium dodecyl sulfate.

25. A process of claim 16, wherein the renaturation solution comprises potassium acetate and sodium chloride.

26. A process of claim 23, wherein the lysis solution contains equal volumes of phenol and chloroform.

27. A process of claim 16, wherein the nucleic acid fragment obtained from the plasmid DNA is immobilized to a solid support prior to detection by mass spectrometry.

28. A process of claim 27, wherein the solid support is a filter membrane or microtiter plate.

29. A process of claim 27, wherein the attachment is reversible.

30. A process of claim 16, wherein, prior to analysis by mass spectrometry, the DNA or nucleic acid fragment has been conditioned whereby the laser energy required for volatization is decreased and/or fragmentation is minimized.

31. A process of claim 30, wherein the conditioning includes a modification of the phosphodiester backbone of the nucleic acid fragment or incorporation of nucleotides which reduce sensitivity for depurination, into the nucleic acid fragment.

32. A process of claim 31, wherein the modification of the phosphodiester backbone of the nucleic acid fragment comprises contacting the nucleic acid with an alkylating agent.

33. A process of claim 31, wherein the nucleotides which reduce sensitivity for depurination comprise N7- or N9-deazapurine nucleotides.

34. A process of claim 31, wherein the modification of the phosphodiester backbone comprises cation exchange.

35. A process of claim 16, wherein prior to step vii), an amplification step is performed on the nucleic acid fragment.

36. A process of claim 35, wherein the amplification step is selected from the group consisting of: the polymerase chain reaction (PCR), the ligase chain reaction (LCR), strand displacement amplification (SDA) and variations thereof.

37. A high throughput method, comprising the steps of:

i) growing plasmid containing cells wherein the plasmids comprise DNA to be sequenced;

ii) washing plasmid-containing cells by filtration with a wash solution to disrupt the cell membrane and degrade RNA;

iii) incubating the resulting washed plasmid containing cells with a lysis/denaturation solution to lyse the cells and denature DNA;

iv) incubating the product of step c) with a renaturation solution for an appropriate period of time and at an appropriate temperature to yield a renatured mixture containing dissolved plasmid DNA, insoluble linear DNA and cellular debris;

v) filtering the product of step d) to obtain a filtrate from which insoluble linear DNA and cellular debris have been removed;

vi) obtaining plasmid DNA from the filtrate; and vii) sequencing the plasmid DNA or a nucleic acid fragment obtained from the plasmid DNA, whereby a plurality of plasmid samples are sequenced.

* * * * *

UNITED STATES PATENT AND TRADEMARK OFFICE
CERTIFICATE OF CORRECTION

PATENT NO. : 6,146,854
DATED : November 14, 2000
INVENTOR(S) : Köster et al.

It is certified that error appears in the above-identified patent and that said Letters Patent is hereby corrected as shown below:

Title page,
Item [75] Inventor, replace "Concord, Mass.;" with -- La Jolla, Calif.; --

Column 8,
Line 48, replace "22a" with -- 224 --
Line 65, replace "filitrate" with -- filtrate --

Column 13, claim 16,
Line 26, should read as the following:
16. A high throughput DNA sequencing method, comprising the steps of :
i) growing plasmid containing cells wherein the plasmids comprise DNA to be sequenced;
ii) washing plasmid-containing cells by filtration with a wash solution to disrupt the cell membrane and degrade RNA;
iii) incubating the resulting washed plasmid containing cells with a lysis/denaturation solution to lyse the cells and denature DNA;
iv) incubating the product of step iii) with a renaturation solution for an appropriate period of time and at an appropriate temperature to yield a renatured mixture containing dissolved plasmid DNA, insoluble linear DNA and cellular debris;
v) filtering the product of step iv) to obtain a filtrate from which insoluble linear DNA and cellular debris have been removed;
vi) obtaining plasmid DNA from the filtrate; and
vii) analyzing a nucleic acid fragment obtained from the plasmid DNA by mass spectrometry to determine the sequence of the fragment of DNA of the plasmid.

Column 13, claim 18,
Line 51, should read as the following:
18. A process of claim 17, wherein prior to step ii), plasmid-containing cells are grown in the wells of the multi-well filter plate.

UNITED STATES PATENT AND TRADEMARK OFFICE
CERTIFICATE OF CORRECTION

PATENT NO. : 6,146,854
DATED : November 14, 2000
INVENTOR(S) : Köster et al.

It is certified that error appears in the above-identified patent and that said Letters Patent is hereby corrected as shown below:

<u>Column 14, claim 37,</u>
Line 42, should read as following:
37. A high throughput method, comprising the steps of:
    i) growing plasmid containing cells wherein the plasmids comprise DNA to be sequenced;
    ii) washing plasmid-containing cells by filtration with a wash solution to disrupt the cell membrane and degrade RNA;
    iii) incubating the resulting washing plasmid containing cells with a lysis/denaturation solution to lyse the cells and denature DNA;
    iv) incubating the product of step <u>iii)</u> with a renaturation solution for an appropriate period of time and at an appropriate temperature to yield a renatured mixture containing dissolved plasmid DNA, insoluble linear DNA and cellular debris;
    v) filtering the product of step <u>iv)</u> to obtain a filtrate from which insoluble linear DNA and cellular debris have been removed;
    vi) obtaining plasmid DNA from the filtrate; and
    vii) sequencing the plasmid DNA or a nucleic acid fragment obtained from the plasmid DNA, whereby a plurality of plasmid samples are sequenced.

Signed and Sealed this

First Day of January, 2002

*Attest:*

*Attesting Officer*

JAMES E. ROGAN
*Director of the United States Patent and Trademark Office*